United States Patent
Dikeman et al.

(10) Patent No.: US 8,172,807 B2
(45) Date of Patent: *May 8, 2012

(54) INTRAVENOUS SECUREMENT DEVICE WITH ADHESIVELY INTERCONNECTED ANCHORING COMPONENT AND PERMEABLE ADHESIVE STRIP

(75) Inventors: W. Cary Dikeman, Leawood, KS (US); Chris Winsor, Olathe, KS (US); Steve A. Cash, Overland Park, KS (US); Larry C. Smith, Shawnee, KS (US)

(73) Assignee: Venetec International, Inc., Covington, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/191,314

(22) Filed: Jul. 26, 2011

(65) Prior Publication Data
US 2011/0282294 A1 Nov. 17, 2011

Related U.S. Application Data

(63) Continuation of application No. 12/871,542, filed on Aug. 30, 2010, now Pat. No. 7,985,206, which is a continuation of application No. 11/457,279, filed on Jul. 13, 2006, now Pat. No. 7,806,873.

(51) Int. Cl.
*A61M 5/32* (2006.01)

(52) U.S. Cl. ............................................. 604/180

(58) Field of Classification Search ............ 604/180, 604/174, 539, 177
See application file for complete search history.

(56) References Cited

U.S. PATENT DOCUMENTS

| | | | |
|---|---|---|---|
| 2,525,398 | A | 10/1950 | Collins |
| 2,553,961 | A | 12/1950 | Rousseau et al. |
| 2,707,953 | A | 5/1955 | Ryan |
| 3,059,645 | A | 10/1962 | Hasbrouck et al. |
| 3,064,648 | A | 11/1962 | Bujan |
| 3,167,072 | A | 1/1965 | Stone et al. |
| 3,204,636 | A | 9/1965 | Kariher et al. |
| 3,256,880 | A | 6/1966 | Caypinar |
| 3,289,671 | A | 12/1966 | Troutman et al. |
| 3,482,569 | A | 12/1969 | Raaelli, Sr. |
| 3,524,443 | A | 8/1970 | Batlin |
| 3,529,597 | A | 9/1970 | Fuzak |

(Continued)

FOREIGN PATENT DOCUMENTS

CA 0995995 8/1976

(Continued)

OTHER PUBLICATIONS

3M Technical Data Sheet entitled "Adhesive Transfer Tapes with Adhesive 300MP 9692-9695-964" (Sep. 2002).

(Continued)

*Primary Examiner* — Nicholas Lucchesi
*Assistant Examiner* — Brooke Matney
(74) *Attorney, Agent, or Firm* — Knobbe Martens Olson & Bear, LLP (57) ABSTRACT

A catheter anchoring assembly includes a permeable adhesive strip, a platform for securing the catheter, and a flowable adhesive layer. The flowable adhesive layer adhesively secures the platform to the adhesive strip. The flowable adhesive is applied to one side of the strip with a skin-contacting adhesive on the opposite side of the strip. The flowable adhesive layer and strip are configured so that the flowable adhesive is spaced from the skin-contacting adhesive or, at the very least, is prevented from penetrating the skin-contacting adhesive. The flowable adhesive layer and strip also permit the assembly to be very flexible and, thus, comfortable for a patient to wear.

20 Claims, 3 Drawing Sheets

U.S. PATENT DOCUMENTS

| | | |
|---|---|---|
| 3,542,321 A | 11/1970 | Kahabka |
| 3,602,227 A | 8/1971 | Andrew |
| 3,630,195 A | 12/1971 | Santomieri |
| 3,632,071 A | 1/1972 | Cameron et al. |
| 3,677,250 A | 7/1972 | Thomas |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,906,946 A | 9/1975 | Nordstrom |
| 3,942,228 A | 3/1976 | Buckman et al. |
| 3,942,750 A | 3/1976 | Noorily |
| 3,973,656 A | 8/1976 | Steer |
| 3,993,081 A | 11/1976 | Cussell |
| 4,020,835 A | 5/1977 | Nordstrom et al. |
| 4,030,540 A | 6/1977 | Roma |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,114,626 A | 9/1978 | Beran |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,353,369 A | 10/1982 | Muetterties et al. |
| 4,362,156 A | 12/1982 | Feller, Jr. et al. |
| 4,392,853 A | 7/1983 | Muto |
| 4,392,857 A | 7/1983 | Beran |
| 4,397,647 A | 8/1983 | Gordon |
| 4,442,994 A | 4/1984 | Logsdon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,484,913 A | 11/1984 | Swauger |
| 4,498,903 A | 2/1985 | Mathew |
| 4,516,293 A | 5/1985 | Beran |
| 4,516,968 A | 5/1985 | Marshall et al. |
| 4,517,971 A | 5/1985 | Sorbonne |
| 4,563,177 A | 1/1986 | Kamen |
| 4,617,017 A | 10/1986 | Hubbard et al. |
| 4,623,102 A | 11/1986 | Hough, Jr. |
| 4,633,863 A | 1/1987 | Filips et al. |
| 4,650,473 A | 3/1987 | Bartholomew et al. |
| 4,660,555 A | 4/1987 | Payton |
| 4,669,156 A | 6/1987 | Goido et al. |
| 4,711,636 A | 12/1987 | Bierman |
| D293,717 S | 1/1988 | Proulx et al. |
| 4,737,143 A | 4/1988 | Russell |
| 4,742,824 A | 5/1988 | Payton et al. |
| 4,762,513 A | 8/1988 | Choy et al. |
| 4,775,121 A | 10/1988 | Carty |
| 4,791,164 A | 12/1988 | Wichelhaus et al. |
| 4,808,162 A | 2/1989 | Oliver |
| 4,823,789 A | 4/1989 | Beisang, III |
| 4,826,486 A | 5/1989 | Paisrok et al. |
| 4,828,549 A | 5/1989 | Kvalo |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,881,705 A | 11/1989 | Kraus |
| 4,896,465 A | 1/1990 | Rhodes et al. |
| 4,897,082 A | 1/1990 | Erskine |
| 4,898,587 A | 2/1990 | Mera |
| 4,899,963 A | 2/1990 | Murphy |
| 4,919,654 A | 4/1990 | Kalt |
| D308,576 S | 6/1990 | Iversen |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,078,731 A | 1/1992 | Hayhurst |
| 5,084,026 A | 1/1992 | Shapiro |
| 5,098,399 A | 3/1992 | Tollini |
| 5,112,313 A | 5/1992 | Sallee |
| 5,147,322 A | 9/1992 | Bowen et al. |
| 5,156,641 A | 10/1992 | White |
| 5,163,914 A | 11/1992 | Abel |
| 5,192,273 A | 3/1993 | Bierman |
| 5,192,274 A | 3/1993 | Bierman |
| 5,195,981 A | 3/1993 | Johnson |
| 5,226,892 A | 7/1993 | Boswell |
| 5,234,185 A | 8/1993 | Hoffman et al. |
| 5,257,768 A | 11/1993 | Juenemann et al. |
| 5,263,943 A | 11/1993 | Vanderbrock |
| 5,266,401 A | 11/1993 | Tollini |
| 5,267,967 A | 12/1993 | Schneider |
| 5,280,866 A | 1/1994 | Ueki |
| 5,282,463 A | 2/1994 | Hammersley |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,314,411 A | 5/1994 | Bierman et al. |
| 5,318,546 A | 6/1994 | Bierman |
| 5,322,514 A | 6/1994 | Steube et al. |
| 5,330,438 A | 7/1994 | Gollobin et al. |
| 5,334,186 A | 8/1994 | Alexander |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,374,254 A | 12/1994 | Buma |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang et al. |
| 5,397,639 A | 3/1995 | Tollini |
| 5,403,285 A | 4/1995 | Roberts |
| 5,413,562 A | 5/1995 | Swauger |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gerbert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,474,572 A | 12/1995 | Hayhurst |
| 5,484,420 A | 1/1996 | Russo |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,549,567 A | 8/1996 | Wolman |
| D375,355 S | 11/1996 | Bierman |
| D375,356 S | 11/1996 | Bierman |

| | | |
|---|---|---|
| 5,578,013 A | 11/1996 | Bierman |
| D377,831 S | 2/1997 | Bierman |
| 5,613,655 A | 3/1997 | Marion |
| 5,616,135 A | 4/1997 | Thorne et al. |
| 5,629,063 A | 5/1997 | Gobran |
| 5,637,098 A | 6/1997 | Bierman |
| 5,653,411 A | 8/1997 | Picco et al. |
| 5,670,234 A | 9/1997 | Suehr et al. |
| 5,693,032 A | 12/1997 | Bierman |
| 5,697,907 A | 12/1997 | Gaba |
| 5,702,371 A | 12/1997 | Bierman |
| D389,911 S | 1/1998 | Bierman |
| 5,722,959 A | 3/1998 | Bierman |
| D393,903 S | 4/1998 | Bierman |
| 5,738,660 A | 4/1998 | Luther |
| 5,785,201 A | 7/1998 | Bordner et al. |
| 5,795,335 A | 8/1998 | Zinreich |
| 5,800,402 A | 9/1998 | Bierman |
| 5,810,781 A | 9/1998 | Bierman |
| D399,954 S | 10/1998 | Bierman |
| D401,329 S | 11/1998 | Bierman |
| 5,833,663 A | 11/1998 | Bierman et al. |
| D404,815 S | 1/1999 | Bierman |
| 5,921,991 A | 7/1999 | Whitehead et al. |
| 5,941,263 A | 8/1999 | Bierman |
| 5,944,696 A | 8/1999 | Bayless et al. |
| 6,001,081 A | 12/1999 | Collen |
| 6,024,761 A | 2/2000 | Barone et al. |
| 6,027,480 A | 2/2000 | Davis et al. |
| D425,619 S | 5/2000 | Bierman |
| 6,117,163 A | 9/2000 | Bierman |
| 6,132,398 A | 10/2000 | Bierman |
| 6,213,979 B1 | 4/2001 | Bierman |
| 6,224,571 B1 | 5/2001 | Bierman |
| 6,274,786 B1 | 8/2001 | Heller |
| 6,283,945 B1 | 9/2001 | Bierman |
| 6,290,676 B1 | 9/2001 | Bierman |
| 6,332,874 B1 | 12/2001 | Eliasen et al. |
| 6,361,523 B1 | 3/2002 | Bierman |
| 6,413,240 B1 | 7/2002 | Bierman et al. |
| 6,428,515 B1 | 8/2002 | Bierman et al. |
| 6,447,485 B2 | 9/2002 | Bierman |
| 6,458,104 B2 | 10/2002 | Gautsche |
| 6,491,664 B2 | 12/2002 | Bierman |
| D470,936 S | 2/2003 | Bierman |
| 6,551,285 B1 | 4/2003 | Bierman |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,663,600 B2 | 12/2003 | Bierman et al. |
| 6,685,670 B2 | 2/2004 | Miles et al. |
| D492,411 S | 6/2004 | Bierman |
| 6,770,055 B2 | 8/2004 | Bierman et al. |
| 6,786,892 B2 | 9/2004 | Bierman |
| 6,796,310 B2 | 9/2004 | Bierman |
| 6,829,705 B2 | 12/2004 | Smith |
| 6,837,875 B1 | 1/2005 | Bierman |
| 6,872,194 B2 | 3/2005 | Doyle et al. |
| D503,977 S | 4/2005 | Bierman |
| 6,984,145 B1 | 1/2006 | Lim et al. |
| 7,320,681 B2 | 1/2008 | Gillis et al. |
| 7,354,421 B2 | 4/2008 | Bierman |
| 2002/0026152 A1 | 2/2002 | Bierman |
| 2003/0125668 A1 | 7/2003 | Bierman |
| 2004/0167475 A1 | 8/2004 | Wright et al. |
| 2005/0205708 A1 | 9/2005 | Sasaki et al. |

FOREIGN PATENT DOCUMENTS

| | | |
|---|---|---|
| CA | 2281457 | 2/2001 |
| DE | 2341297 | 8/1973 |
| DE | 4000380 | 1/1990 |
| DE | 29608294 | 8/1996 |
| EP | 0064284 | 4/1982 |
| EP | 0247590 | 12/1987 |
| EP | 0597213 | 5/1994 |
| EP | 0356683 | 3/2000 |
| FR | 1184139 | 7/1959 |
| FR | 2381529 | 9/1978 |
| FR | 2722414 | 7/1994 |
| FR | 2852520 | 3/2003 |
| GB | 2063679 | 6/1981 |
| GB | 2086466 | 5/1982 |
| GB | 2312619 | 10/1997 |
| JP | 06063153 | 3/1994 |
| JP | 06208572 | 7/1994 |
| JP | 08024344 | 1/1996 |
| JP | 08182492 | 7/1996 |
| WO | WO 8001458 | 7/1980 |
| WO | WO 8502774 | 7/1985 |
| WO | WO 9116939 | 11/1991 |
| WO | WO 9219309 | 11/1992 |
| WO | WO 9610435 | 4/1996 |
| WO | WO 9626756 | 9/1996 |
| WO | WO 2007/028007 | 3/2007 |

OTHER PUBLICATIONS

Bostik Findley Product Data Sheet entitled "4229 Hot Melt Adhesives" (Sep. 2003).

Brief in Support of Nexus Medical, LLC's Motion for Summary Judgement of Noninfringement of the Venetec Patents (Public Redacted Version); *Venetec International Inc.* v. *Nexus Medical, LLC*, U.S. District Court for Delaware, Case No. 07-CV-0057***, Public version filed Oct. 24, 2008, 158 pages.

Brief in Support of Nexus Medical, LLC's Motion for Summary Judgement that the Venetec Patents are Invalid; Filed Oct. 10, 2008; *Venetec International Inc.* v. *Mexus Medical, LLC*, USDC, District of Delaware, Civil Action No. 07-cv-0057-MPT.

Civil Docket for Case No. 1:07-CV-00057*** [printed Oct. 22, 2007].

Complaint [dated Jan. 29, 2007] *Venetec Intl, Inc.* v. *Nexus Medical, LLC*, USDC D.Del., Case No. 1:07-CV-00057***.

Declaration of Jennifer C. Bailey in Support of Nexus' Opposition to Venetec's Motion for Partial Judgement on the Pleadings, *Venetec International Inc.* v. *Nexus Medical, LLC*, U.S. District Court for Delaware, Case No. 07-CV-0057***, 31 pgs.

Defendant Nexus Medical, LLC's Objections and Responses to Plaintiff Venetec International, Inc's Modified and Supplemental Definitions Set Forth in its First Set of Interrogatories to Defendant Nexus Medical, LLC, *Venetec International, Inc.* v. *Nexus Medical, LLC*, U.S. District Court for Delaware, Case No. 07-CV-0057***, 79 pgs.

Defendant Nexus Medical, LLC's Reply to Plaintiff's Answering Brief in Opposition to Defendant's Motion for Summary Judgement of Invalidity; Filed: Nov. 10, 2008; *Venetec International, Inc.*, v. *Nexus Medical, LLC*; USDC, District of Delaware, Civil Action No. 07-cv-0057-MPT.

Defendant Nexus Medical, LLC's Reply to Plaintiff's Answering Brief in Opposition to Defendant's Motion for Summary Judgement of Noninfringement of the Venetec Patents (Public Version); *Venetec International Inc.* v. *Nexus Medical, LLC*, U.S. District Court for Delaware, Case No. 07-CV-0057***, Public version filed Nov. 18, 2008, 27 pgs.

Expert Report of Julie E. Shomo Regarding Invalidity of the Venetec Patents Pursuant to Rule 26(a)(2)(B), *Venetec International Inc.* v. *Nexus Medical, LLC*, U.S. District Court for Delaware, Case No. 07-CV-0057***, Jul. 18, 2008, 31 pgs.

Expert Report of Marvin Gordon Regarding Invalidity of the Venetec Patents Pursuant to Rule 26(a)(2)(B), *Venetec International Inc.* v. *Nexus Medical, LLC*, U.S. District Court for Delaware, Case No. 07-CV-0057***, Jul. 18, 2008, 23 pgs.

Expert Report of William H. Hirsch Regarding Invalidity of the Venetec Patents Pursuant to Rule 26(a)(2)(B), *Venetec International Inc.* v. *Nexus Medical, LLC*, U.S. District Court for Delaware, Case No. 07-CV-0057***, Jul. 18, 2008, 39 pgs.

First Supplemental Complaint [dated Jul. 24, 2007]. *Venetec Int'l, Inc.* v. *Nexus Medical, LLC*, USDC D.Del., Case No. 1:07-CV-00057***.

Hi-Tech Products Material Data Sheet entitled "Tricot PSA" (printed prior to Jul. 13, 2006).

Interview Summary in the Ex Parte Reexamination of the '150 patent, U.S. Appl. No. 90/010,211, mailed Dec. 19, 2008, 3 pgs.

Interview Summary in the Ex Parte Reexamination of the '979 patent, U.S. Appl. No. 90/010,167, mailed Dec. 19, 2008, 4 pgs.

Joint Claim Construction Chart; *Venetec International Inc. v. Nexus Medical, LLC*, U.S. District Court for Delaware, Case No. 07-CV-0057***, Oct. 10, 2008, 91 pgs.

Judge Thynge's Order Denying Nexus Motion to Stay Proceedings Pending Reexamination, *Venetec International Inc. v. Nexus Medical, LLC*, U.S. District Court for Delaware, Case No. 07-CV-0057***, 1 pg.

Memorandum Order; *Venetec International Inc. v. Nexus Medical, LLC*, U.S. District Court for Delaware, Case No. 07-CV-0057***, Mar. 28, 2008, 16 pgs.

Nexus Medical LLC's Opening Claim Construction Brief; *Venetec International Inc. v. Nexus Medical, LLC*, U.S. District Court for Delaware, Case No. 07-CV-0057***, Oct. 10, 2008, 142 pgs.

Nexus Medical, LLC's Answer to Venetec International, Inc.'s Complaint and Counterclaim [dated Mar. 22, 2007]. *Venetec Intl, Inc. v. Nexus Medical, LLC*, USDC D.Del., Case No. 1:07-CV-00057***.

Nexus Medical, LLC's Answer to Venetec International, Inc.'s Second Supplemental Complaint and Counterclaim [filed Sep. 19, 2007]. *Venetec Int'l, Inc. v. Nexus Medical, LLC*, USDC D.Del., Case No. 1:07-CV-00057***.

Nexus Medical, LLC's Answer to Venetec International, Inc's First Supplemental Complaint and Counterclaim [dated Aug. 8, 2007]. *Venetec Int'l, Inc. v. Nexus Medical, LLC*, USDC D.Del., Case No. 1:07-CV-00058***.

Nexus Medical, LLC's First Amended Answer and Counterclaim to Venetec International, Inc.'s Second Supplemental Complaint and Counterclaim; *Venetec International Inc. v. Nexus Medical, LLC*, U.S. District Court for Delaware, Case No. 07-CV-0057***, 50 pgs.

Nexus Medical, LLC's Objections and Responses to Venetec International, Inc's First Set of Interrogatories, *Venetec International Inc. v. Nexus Medical, LLC*, U.S. District Court for Delaware Case No. 07-CV-0057***, pp. 1-47.

Nexus' letter to Judge Thynge dated Sep. 28, 2007, *Venetec International Inc. v. Nexus Medical, LLC*, U.S. District Court for Delaware, Case No. 07-CV-0057***, 2 pgs.

Nexus' Opposition to Venetec's Motion for Partial Judgement on the Pleadings, *Venetec International Inc. v. Nexus Medical, LLC*, U.S. District Court for Delaware, Case No. 07-CV-0057***, 28 pgs.

Notice of Assignment of Inter Partes Reexamination Request for the '485 patent, *Venetec International Inc. v. Nexus Medical, LLC*, U.S. District Court for Delaware, Case No. 07-CV-0057***, 1 pg.

Notice of Assignment of Reexamination, U.S. Appl. No. 90/010,211, mailed Jul. 7, 2008, 1 pg.

Notice of Reexamination Request Filing Date, U.S. Appl. No. 90/010,211, mailed Jul. 7, 2008, 1 pg.

Office Action in the Ex Parte Reexamination of the '150 patent, U.S. Appl. No. 90/010,211, dated May 11, 2009.

Office Action in the Ex Parte Reexamination of the '979 patent, U.S. Appl. No. 90/010,167, dated May 8, 2009.

Office Action issued to Venetec in the Ex Parte Reexamination of the '150 patent, U.S. Appl. No. 90/010,211, mailed Nov. 7, 2008, 20 pgs.

Office Action Issued to Venetec in the Ex Parte Reexamination of the '979 patent, U.S. Appl. No. 90/010,167, mailed Nov. 7, 2008, 21 pgs.

Office Action issued to Venetec in the Inter Partes Reexamination, *Venetec International Inc. v. Nexus Medical*, U.S. District Court for Delaware, Case No. 07-CV-0057***, 23 pgs.

Order Granting Inter Partes Reexamination, *Venetec International Inc. v. Nexus Medical, LLC*, U.S. District Court for Delaware, Case No. 07-CV-0057***, 29 pgs.

Order Granting Request for Ex Parte Reexamination of the '150 patent, U.S. Appl. No. 90/010,211, mailed Jul. 29, 2008, 16 pgs.

Order Granting Request for Ex Partes Reexamination, Ex Parte Reexamination of the '979 patent, U.S. Appl. No. 90/010,167, Jul. 29, 2008, 14 pgs.

Order Granting Request for Inter Partes Reexamination & Reexamination Non-Final Office Action, Inter Partes Reexamination No. 95/000271, Sep. 21, 2007, 50 pgs.

Patent Owner's Response to Office Action issued to Venetec in the Ex Parte Reexamination of the '150 patent, U.S. Appl. No. 90/010,121, Jan. 7, 2009, 36 pgs.

Patent Owner's Response to Office Action issued to Venetec in the Ex Parte Reexamination of the '979 patent, U.S. Appl. No. 90/010,167, Jan. 7, 2009, 42 pgs.

Patent Owner's Response to Office Action, Inter Partes Reexamination No. 95/000271, Nov. 21, 2007, 90 pgs.

Patent Owner's Supplemental Response to Office Action, Inter Partes Reexamination No. 95/000271, Dec. 21, 2007, 46 pgs.

Patent Owner's Supplemental Response to Office Action, Inter Partes Reexamination No. 95/00271, Sep. 29, 2008, 46 pgs.

Plaintiff's Answering Brief in Opposition to Defendant's Motion for Summary Judgement of invalidity; Filed: Oct. 30, 2008; *Venetec International, Inc., v. Nexus Medical, LLC*; USDC, District of Delaware, Civil Action No. 07-cv-0057-MPT.

Plaintiff's Opening Claim Construction Brief; *Venetec International Inc. v. Nexus Medical, LLC*, U.S. District Court for Delaware, Case No. 07-CV-0057***, Oct. 10, 2008, 45 pgs.

Rebuttal Expert Report of Dr. Terry N. Layton, Ph.D., *Venetec International Inc. v. Nexus Medical, LLC*, U.S. District Court for Delaware, Case No. 07-CV-0057***, Aug. 29, 2008, 33 pgs.

Request for Inter Partes Reexamination Under 37 C.F.R. 1.913 [filed Jun. 25, 2007]. In re Bierman, USPTO, Reexamination No. 95/000,271.

Second Supplemental Complaint [filed Sep. 5, 2007]. *Venetec Int'l, Inc. v. Nexus Medical, LLC*, USDC D.Del., Case No. 1:07-CV-00057***.

Stipulation and Order amending Nexus Medical, LLC's Answer to Complaint and Counterclaim, *Venetec International Inc. v. Nexus Medical, LLC*, U.S. District Court for Delaware, Case No. 07-CV-0057***, 15 pgs.

Third-Party Requester's Response to Patent Owner's Response to Office Action Dated Sep. 21, 2007, Inter Partes Reexamination No. 95/000271, Dec. 21, 2007, 85 pages.

Third-Party Requester's Supplemental Response to Patent Owner's Supplemental Response to Patent Owner's Supplemental Response to Office Action Dated Sep. 21, 2007, Inter Partes Reexaminaton No. 95/000271, Jan. 22, 2008, 48 pgs.

Transcript of Claim Construction Hearing; *Venetec International Inc. v. Nexus Medical, LLC*, U.S. District Court for Delaware, Case No. 07-CV-0057***, Nov. 21, 2008, 70 pgs.

Tri-State Hospital Supply Corporation, Centurion Healthcare Products brochure for HubGuard Catheter Securement (Mar. 3, 2004).

Tri-State Hospital Supply Corporation, Centurion Healthcare Products brochure for IV start Kits (Sep. 14, 2004).

Tri-State Hospital Supply Corporation, Centurion Healthcare Products brochure for LineGuard J-Loop Securement Device (Nov. 2, 2004).

Tri-State Hospital Supply Corporation, Centurion Healthcare Products brochure for Port Access Trays (Apr. 24, 2003).

Tri-State Hospital Supply Corporation, Centurion Healthcare Products brochure for SorbaView 2000 Window Dressing (Apr. 14, 2004).

Tri-State Hospital Supply Corporation, Centurion Healthcare Products brochure for SorbaView Ultimate Window Dressing (May 7, 2004, Jun. 22, 2004).

Venetec International, Inc.'s Reply to Nexus Medical, LLC's Counterclaim [ filed Apr. 11, 2007]. *Venetec Int'l, Inc. v. Nexus Medical, LLC*, USDC D.Del., Case No. 1:07-CV-00057***.

Venetec International, Inc.'s Reply to Nexus Medical, LLC's Counterclaim [filed Aug. 28, 2007]. *Venetec Int'l, Inc. v. Nexus Medical, LLC*, USDC D.Del., Case No. 1:07-CV-00057***.

Venetec International, Inc.'s Reply to Nexus Medical, LLC's Counterclaim [filed Sep. 27, 2007]. *Venetec Int'l, Inc. v. Nexus Medical, LLC*, USDC D.Del., Case No. 1:07-CV-00057***.

Venetec's letter to Judge Thynge dated Sep. 28, 2007, *Venetec International Inc. v. Nexus Medical, LLC*, U.S. District Court for Delaware, Case No. 07-CV-0057***, 6 pgs.

Venetec's Motion for Partial Judgement on the Pleadings, *Venetec International Inc. v. Nexus Medical, LLC*, U.S. District Court for Delaware, Case No. 07-CV-0057***, 3 pgs.

Venetec's Opening Brief in Support of Motion for Partial Judgement on the Pleadings, *Venetec International Inc. v. Nexus Medical, LLC*, U.S. District Court for Delaware, Case No. 07-CV-0057***, 34 pgs.

Zefon International printout from www.zefon.com/medical/griplok.htm depicting prior art GRIP-LOK Universal Tubing Securement Device (Printed Jun. 20, 2005).

INTRAVENOUS SECUREMENT DEVICE WITH ADHESIVELY INTERCONNECTED ANCHORING COMPONENT AND PERMEABLE ADHESIVE STRIP

RELATED APPLICATIONS

This application is a continuation of copending U.S. patent application Ser. No. 12/871,542 filed on Aug. 30, 2010, entitled "INTRAVENOUS SECUREMENT DEVICE WITH ADHESIVELY INTERCONNECTED ANCHORING COMPONENT AND PERMEABLE ADHESIVE STRIP," which is a continuation of U.S. patent application Ser. No. 11/457,279 filed on Jul. 13, 2006, now U.S. Pat. No. 7,806,873 issued on Oct. 5, 2010, entitled "INTRAVENOUS SECUREMENT DEVICE WITH ADHESIVELY INTERCONNECTED ANCHORING COMPONENT AND PERMEABLE ADHESIVE STRIP," each of which is hereby expressly incorporated by reference in its entirety.

BACKGROUND OF THE INVENTION

1. Field of the Invention

The present invention relates generally to the field of intravenous infusion site devices. More specifically, the present invention concerns an intravenous catheter anchoring device with an adhesively interconnected anchoring component and permeable adhesive strip for the securement of catheters on various infusion sites.

2. Discussion of Prior Art

Catheters for intravenous infusion into a patient are well known in the art. Such catheters are generally used in a variety of infusion applications and on a variety of sites. For example, catheters are commonly used as central venous catheters ("CVC"), midline catheters, or peripherally inserted central catheters ("PICC"). Secure positioning of the catheter is important because precise catheter location within the venous system is normally critical.

One prior art technique for securing the catheter in place involves the use of tape wrapped around the catheter and adhered to the patient. A significant problem associated with this technique is the increased risk of bloodstream infections, which typically require expensive and extended antibiotic therapy and can, in some instances, cause death. In particular, the securement tape is typically not sterile and securement generally can harbor bacteria. Furthermore, tape typically does not sufficiently prevent axial catheter movement in and out of the venipuncture site (i.e., catheter pistoning). Therefore, any bacteria on the catheter itself can be introduced into the bloodstream by pistoning of the catheter into the venipuncture site. Some prior art securement devices are sutured onto the patient and these present an additional path for introducing bacteria into the bloodstream.

Consequently, securement devices have been developed for attaching the catheter to the patient. The securement device usually includes a tape that adheres to the patient's skin and a catheter retaining structure attached to the tape. The securement device typically includes a release liner covering the skin-contacting side of the tape, with the liner being removed prior to application of the device. The securement device is preferably designed for various applications and can be used to secure catheters at various locations on the patient's body. In particular, the securement device must be able to adhere itself and conform to contoured surfaces including the patient's torso (in the case of a CVC) as well as the patient's arm (in the case of a PICC). Moreover, patients with these catheters often want or need to have a normal range of body motion while the catheter is inserted and be comfortable while having the catheters secured. Therefore, people have a need for a catheter anchoring device that provides reliable yet comfortable catheter securement during patient movement.

Again, securement devices are often used with catheters to prevent catheter movement. However, these conventional securement devices are problematic and suffer from various undesirable limitations.

Another problem is that the release liner used with these traditional securement devices is generally difficult to remove. Specifically, techniques for attaching the tape to the rest of the device tend to interfere with removal of the release liner.

Yet another problem is that the prior art securement devices are normally uncomfortable to wear. For example, the prior art devices typically use a tape substrate that is relatively stiff and does not conform to the patient during movement. In particular, the prior art devices often use a foam-based substrate that does not readily bend. The prior art substrates also are uncomfortable because they prevent moisture from evaporating from the skin surface, which often results in skin rashes or fungus growth. Foam-based substrates also make it difficult to assess the condition of the patient's skin under the device. This type of material also has a tendency to degrade or delaminate during use, which make dressing changes more difficult and problematic.

Accordingly, there is a need for an improved intravenous catheter anchoring device that does not suffer from these problems and limitations.

SUMMARY OF THE INVENTION

A first aspect of the present invention concerns an intravenous catheter anchoring device for securing a catheter to a patient. The device broadly includes a platform, a flexible and at least partly permeable strip, a release liner, and an attachment layer. The platform is configured to couple to the catheter. The strip includes a plurality of interstices therein and presents first and second opposite surfaces. The strip is configured to be removably attached to the patient along the first surface. The strip includes a skin-contacting adhesive layer adhered to the first surface. The release liner is removably attached to the first surface so that the first surface is at least partly covered by the release liner before the strip is attached to the patient. The attachment layer is located between and adheres the platform and strip along a wetted portion of the second surface. The attachment layer comprises an adhesive material that is flowable prior to being solidified. The attachment layer extends from the wetted portion into at least some of the interstices so that the adhesive material becomes solidified therein. The attachment layer is entirely spaced from the release liner when solidified so that the attachment layer is restricted from adhering the strip to the release liner.

A second aspect of the present invention concerns an intravenous catheter anchoring device for securing a catheter to a patient. The device broadly includes a platform, a flexible and at least partly permeable strip, a release liner, and an attachment layer. The platform is configured to couple to the catheter. The strip presents first and second opposite surfaces. The strip is configured to be removably attached to the patient along the first surface. The platform and strip are formed of different materials. The strip includes a skin-contacting adhesive layer adhered to the first surface. The release liner removably attaches to the first surface so that the first surface is at least partly covered by the release liner before the strip is attached to the patient. The attachment layer is located between and adheres the platform and strip along the second surface. The attachment layer comprises a hot-melt adhesive material.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

Figures 1, 2:
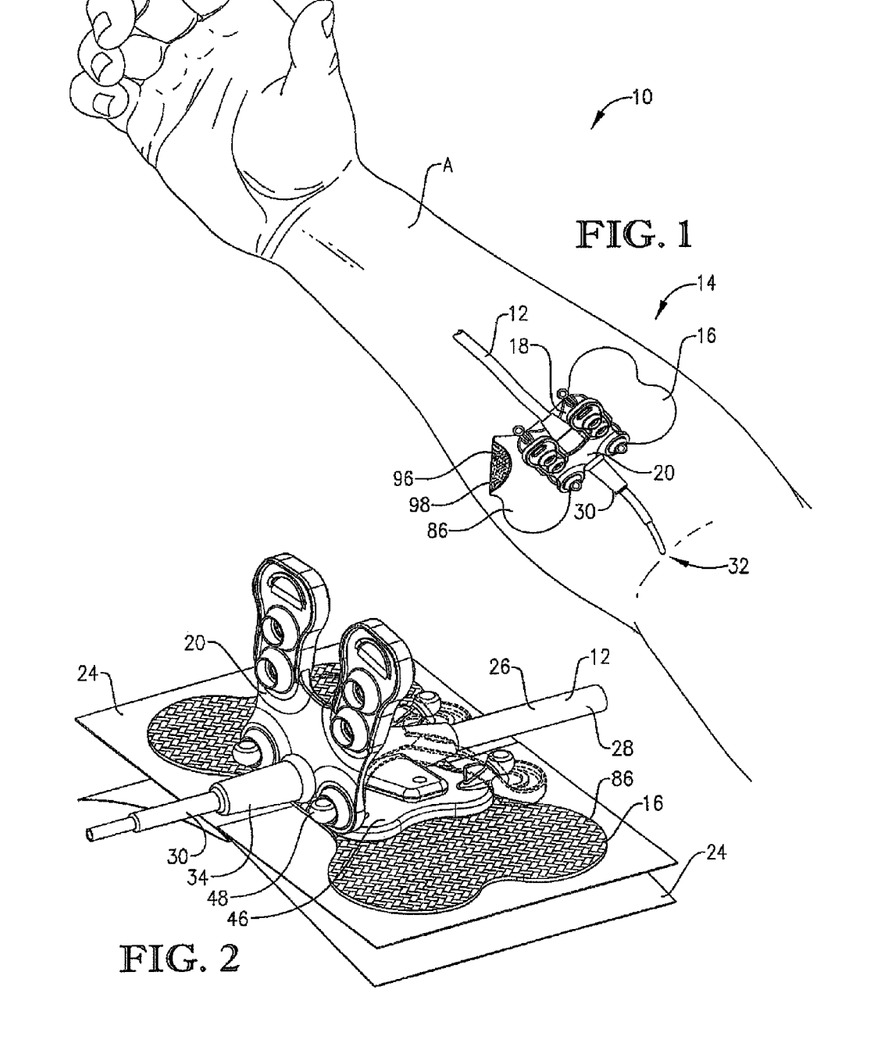
FIG. 1 is a perspective view of an intravenous catheter anchoring device with an adhesively interconnected anchoring component and a permeable adhesive strip constructed in accordance with a preferred embodiment of the present invention and showing the anchoring device attached to a patient's arm such that the anchoring device secures a single-lumen catheter with a suture hub to provide a peripherally inserted central catheter.
FIG. 2 is a perspective view of the intravenous catheter anchoring device of FIG. 1, showing the anchoring device with the secured catheter and a release liner attached to the permeable adhesive strip.

An intravenous catheter anchoring assembly 10 for use in securing a catheter 12 to a patient is illustrated in FIG. 1. The catheter anchoring assembly 10 is combined with the catheter 12 to form an intravenous infusion assembly 14. In the usual manner, the infusion assembly 14 is connected to an intravenous administration set (not shown) and enables convenient and repetitive porting to the patient's internal venous system for intravenous therapy and generally for introducing or removing fluids. More specifically, the illustrated catheter anchoring assembly 10 functions as an intravenous site securement device for removably attaching the catheter 12 to the patient's arm A to prevent localized catheter movement, especially any axial catheter movement, i.e., "pistoning".

As will be shown, another catheter anchoring embodiment disclosed herein functions primarily as a tubing collector which secures the catheter's tubing. Tubing collectors generally permit removable attachment of the tubing of a catheter, an intravenous extension set, or of an intravenous administration set to the patient and principally serve to store an excess length of that tubing. Some tubing collectors permit limited axial tubing movement through the collector.

The illustrated embodiment of FIG. 1 specifically shows the infusion assembly 14 with the catheter 12 secured to the patient's arm A as a PICC. However, the catheter 12 may be used for subcutaneous access other than peripheral blood stream access without departing from the scope of the present invention. That is, the illustrated catheter anchoring assembly 10 provides an external mechanism for stabilizing the catheter's position in various locations on the patient. For example, the catheter anchoring assembly 10 can be used to secure a catheter on a patient's chest (not shown) as a CVC. The catheter anchoring assembly 10 broadly includes a patient-contacting strip 16, a platform 18, a retaining strap 20 removably attached to the platform 18, an intervening adhesive layer 22 (see FIG. 3) between the strip 16 and the platform 18, and release liners 24 (see FIG. 2) removably attached to the strip 16.

Figure 3:
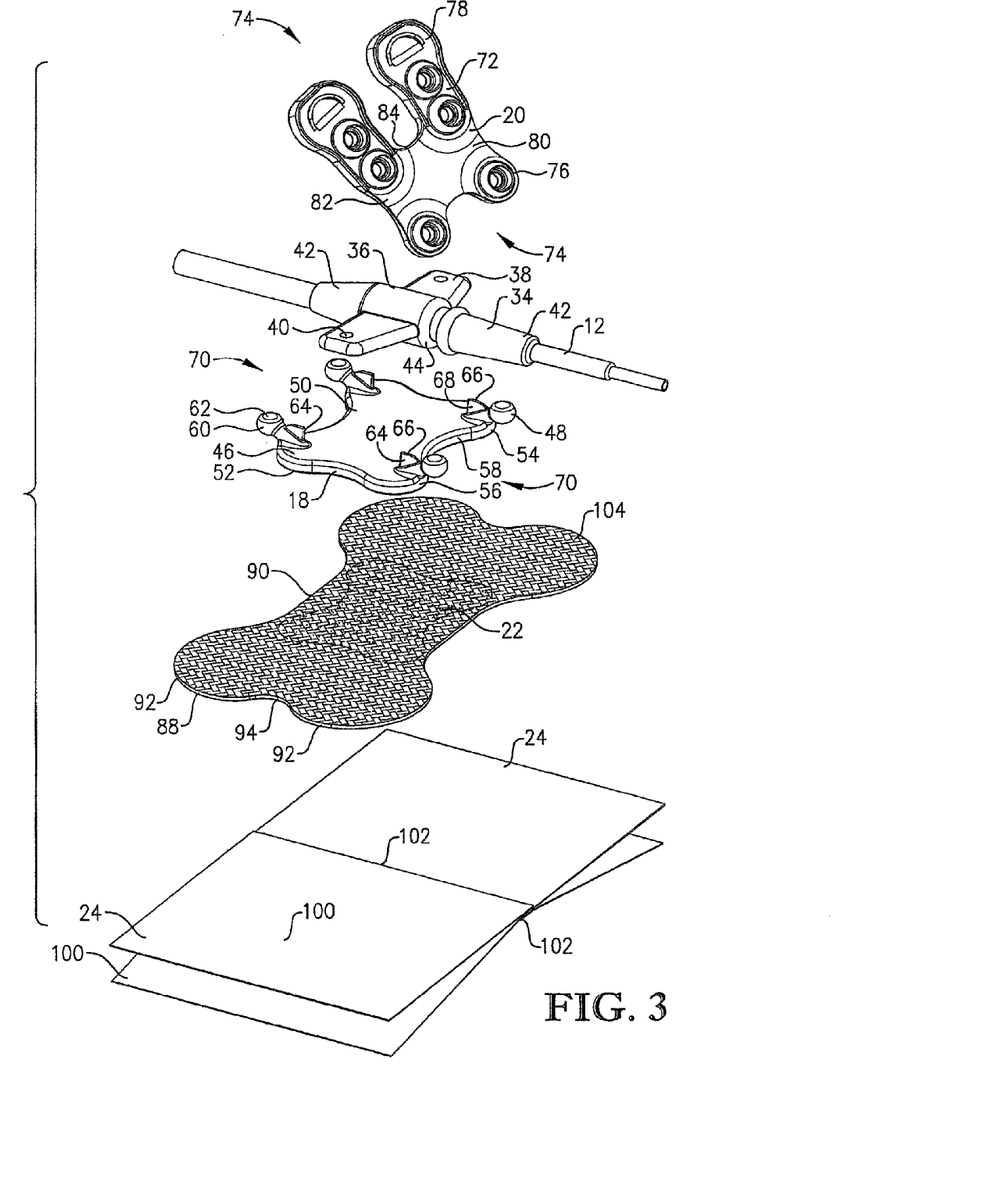
FIG. 3 is an exploded perspective view of the intravenous catheter anchoring device of FIGS. 1 and 2.

Turning to FIGS. 1-3, the catheter 12 permits fluids to be introduced and removed from the patient's venous system. The catheter 12 includes tubing 26 having an internal bore that is also referred to as a lumen (see FIG. 2). The catheter 12 further includes proximal and distal sections 28,30 (with "proximal" and "distal" referring to the relative proximity to the intravenous administration set). As shown in FIG. 1, the distal section 30 extends into and out of the patient's body at a puncture location 32 (sometimes referred to as a venipuncture site). The distal section 30 also terminates (proximally) at a suture hub 34. The proximal section 28 terminates (distally) at the suture hub 34 and at an end (not shown). The proximal and distal sections 28,30 of the PICC catheter 12 each include the single lumen, making the illustrated catheter 12 a single lumen catheter. The lumen is configured in the usual manner to carry fluids to and from the patient. Those ordinarily skilled in the art will appreciate, however, that the use of multiple lumen catheters are entirely within the ambit of the present invention.

As shown particularly in FIG. 3, the suture hub 34 is generally traditional in design and includes a body 36 and oppositely extending wing-shaped projections 38. The projections 38 each include a hole 40 for securing the suture hub 34 with a suture. The body 36 is cylindrically shaped and includes tapered strain relief sections 42 that restrict some bending of the tubing 26 adjacent to the projections 38. The body 36 further includes an annular groove 44 (sometimes referred to as a suture groove). While the above described catheter 12 includes features that are important with respect to some aspects of the present invention, it is entirely consistent with the principles of the present invention to use other types of catheters and catheter anchoring assemblies not depicted in the disclosed embodiments of the infusion assembly 14. Moreover, the present invention is ideally suited for securing a broad range of catheter shapes and sizes, as well as extension sets and administration sets. Some of these alternative catheters and anchoring devices are disclosed in copending application for U.S. patent Ser. No. 11/306,289, filed Dec. 21, 2005, entitled INTRAVENOUS CATHETER ANCHORING DEVICE, which is hereby incorporated by reference herein.

Referring to FIGS. 1-3, the illustrated platform 18 is unitary and includes a base 46 and connectors 48. The base 46 is shaped like a flat plate and includes upper and lower surfaces 50,52 and a contoured edge 54 (see FIG. 3). The contoured edge 54 is formed with rounded corners 56 and recessed scallops 58 between each of the corners 56. The upper and lower surfaces 50,52 are substantially flat and give the base 46 a uniform thickness.

Referring again to FIG. 3, the connectors 48 each include a post 60 having a rounded end 62. Each connector 48 also includes a catch 64 fixed to the corresponding post 60 and extending inwardly and upwardly from the post 60. The catch 64 preferably is a thin plate including a top edge 66 and a side edge 68, and with a thickness that is smaller than the thickness of the post 60. Preferably, the catches 64 extend from the post 60 in a generally inward direction (i.e., from the outer margin of the platform 18 toward the center of the platform 18). More preferably, the catches 64 extend so as to form pairs where the catches 64 are coplanar. However, it is within the ambit of the present invention for the catch 64 to be variously positioned, sized, or include other alternative surfaces for selective engagement with the hub 34 or with other components of the catheter 12. Moreover, consistent with the principles of the present invention, the connectors 48 may be alternatively configured to include more than one catch 64 or other catheter-engaging surface.

As will be described in greater detail, the catches 64 provide surfaces that cooperatively contain and restrict movement of the hub 34 relative to the platform 18. In particular, the side edges 68 are configured to cooperatively trap the suture hub 34 by restricting movement of the projections 38. The side edges 68 restrict movement by extending along an upright direction from the base 46 to the retaining strap 20. In this manner, each pair of adjacent side edges 68 presents an opening with a lateral width that is substantially continuous from the base 46 to the retaining strap 20. Thus, inadvertent twisting or bending of the hub 34 will not permit the projections 38 to slip out of position from between their respective pair of side edges 68. Moreover, the illustrated catches 64 are effective for universally securing virtually all known catheter configurations.

Each of the posts 60 is attached adjacent a respective corner 56 of the base 46 and angles upwardly from the upper surface 50 and away from base 46. A first pair of the connectors 48 extend parallel to each other in a first lateral direction and are similarly angled relative to the base 46 so that they cooperatively define a primary attachment side 70 of the platform 18. A second pair of the connectors 48 also extend parallel to each other and cooperatively form another primary attachment side 70. The second pair are also angled relative to the base 46 at an angle similar to the first pair, but extend in an opposite lateral direction from the first pair. Each of the connectors 48 are spaced apart so that the distance between any two adjacent connectors 48 is about the same (thus forming the corners of an imaginary square).

The connectors 48 and base 46 are preferably injection molded of a relatively hard clear plastic to create the unitary platform 18. Alternatively, the platform 18 can be molded to include a relatively flexible elastomeric insert material (e.g., silicone). Elastomeric materials generally have a lower modulus of elasticity than hard plastic materials and also provide surfaces with a higher coefficient of friction. Therefore, such a material can be incorporated into the platform 18 so that the platform 18 has a surface that grips the catheter 12. Specifically, the elastomeric structure grips the catheter 12 by frictionally engaging and by flexibly conforming to the catheter 12. Additional details of the preferred platform 18 are disclosed in the above incorporated Application.

Turning again to FIGS. 1-3, the catheter anchoring assembly 10 includes the retaining strap 20. The illustrated retaining strap 20 is unitary and is generally elongated and flat. As will be discussed in greater detail, the retaining strap 20 is also preferably flexible and elastomeric (see FIG. 2) to permit frictional engagement with the catheter 12 and to conform to the shape of the catheter 12.

Turning to FIG. 3, the retaining strap 20 includes a body 72. The body 72 includes spaced apart opposite attachment ends 74, each formed by a pair of outwardly extending pull-tabs 76,78, and a centrally located stretch portion 80 between the ends 74. The body 72 presents upper and lower surfaces 82,84. The pull-tabs 76 provide a grasping surface for the retaining strap 20 and each provides an attachment location preferably in the form of a through-hole for receiving a respective one of the connectors 48 as will be discussed. In the preferred embodiment, the pull-tabs 78 are adjustable and have an elongated shape to include three attachment locations, each in the form of through-holes. The pull-tabs 76,78 enable grasping of the retaining strap 20 and further include grasping ribs for that purpose.

The retaining strap 20 includes a substantially homogeneous material. More preferably, the retaining strap 20 is molded out of a substantially clear elastomeric silicon material. Also, the retaining strap 20 is preferably molded in an injection molding process. However, it could also be formed by other molding processes, such as thermoforming, known to those of ordinary skill in the art. Additional details of the preferred retaining strap 20 are disclosed in the incorporated Application.

Figure 4:
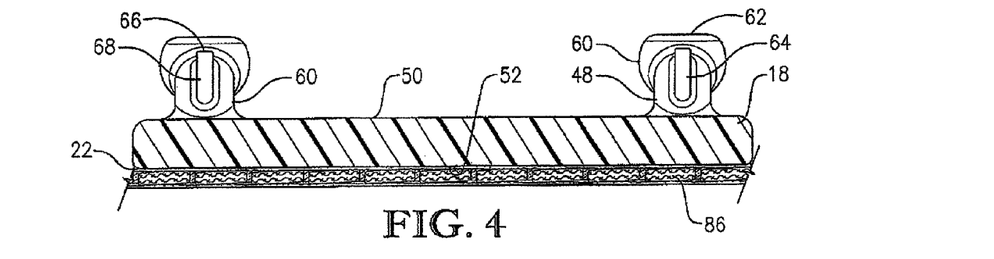
FIG. 4 is a cross-sectional elevational view of the intravenous catheter anchoring device of FIGS. 1-3.

Turning to FIGS. 2-4, the retaining strap 20 is initially attached to the platform 18 by preferably receiving two connectors 48 on one of the platform's sides 64 within respective pull-tabs 76. The rounded end 62 of post 60 is larger in diameter than the hole. Therefore, the elastic pull-tab 76 stretches outwardly so as to pass over end 62 and then be received on the post 60. The undersized hole and rounded end 62 further restrict the pull-tab 76 from becoming unintentionally removed from the attached position. The top edge 66 restricts the pull-tab 76 from lowering to a position adjacent the base 46. In other words, principally along the space between the posts 60, the catches 64 position the attached pull-tabs 76 into a position spaced from the base 46, although such spacing is not necessary and the catches 64 could be alternatively configured to securely hold the catheter 12 but permit the strap 20 to be closer to the platform 18.

In the illustrated embodiment, the retaining strap 20 is fully secured to the platform 18 by lowering the pull-tabs 78 (causing the body 72 to flex as shown in phantom in FIG. 2) so that the remaining two connectors 48 can be received within two of the holes. The upwardly and outwardly angled posts 60 restrict the retaining strap 20 from moving out of the attached position, as the strap 22 would have to be stretched to a greater extent to do so. Furthermore, the top edge 66 restricts the pull-tabs 76,78 from being lowered relative to the posts 60 once the pull-tabs 76,78 are installed thereon. In other words, principally along the space between the posts 60, the catches 64 position the attached pull-tabs 76,78 into a position spaced from the base 46. Thus, the catches 64 also retain the stretch portion 80 of the strap 20 in a position spaced from the base 46. Again, the principles of the present invention are applicable where such spacing is not provided between the strap 20 and base 46 (e.g., where the strap 20 is closely adjacent to the base 46).

As will be discussed, the strap 20, the base 46, and the catches 64 cooperatively contain and restrict movement of the hub 34 relative to the platform 18. As discussed above, the side edges 68 restrict lateral movement by extending along an upright direction from the base 46 to the retaining strap 20. The base 46 and strap 20 cooperatively restrict vertical movement of the hub 34. Furthermore, the base 46, strap 20, and each pair of adjacent side edges 68 present a respective opening with a lateral width between the side edges 68 and a vertical height between the base 46 and strap 20. The illustrated base 46, strap 20, and catches 64 are effective for universally securing virtually all known catheter configurations.

The elastomeric retaining strap 20 preferably includes a lower modulus of elasticity than the platform 18, making the retaining strap 20 less rigid than the platform 18. Therefore, when the retaining strap 20 is attached between connectors 48 under tension, the retaining strap 20 elongates while the platform 18 deflects negligibly. In this manner, the platform substantially retains its shape when the body is elastically stretched to receive the catheter 12.

The catheter anchoring assembly 10 secures the catheter 12 as shown in FIGS. 1-3. In FIGS. 1 and 2, the catheter 12 axis is substantially orthogonal to the longitudinal axis of the strip 16 and platform 18. As discussed, the retaining strap 20 is partially attached to the platform 18 with connectors 48 being received in holes of the tabs 76. In some instances, an edge of the retaining strap 20 is received within the annular groove 44 to further restrict axial movement of the catheter 12.

The pull-tabs 78 are then secured to the remaining connectors 48 by stretching the retaining strap 20 over the suture hub 34. Again, the rounded ends 62 secure the pull-tabs 76,78 onto the posts 60 with the top edge 66 retaining the pull-tabs 76,78 in a position spaced from the base 46 and adjacent the ends 62. The platform 18 and strap 22 are preferably configured and dimensioned so that the strap 22 is elastically stretched when the catheter is secured between the platform 18 and strap 22, whereby the catheter 12 is gripped and axially retained. The suture hub 34 is arranged between the platform 18 and retaining strap 20 with the tubing 26 across the primary attachment sides 70 and extending through oppositely spaced openings (see FIG. 2) cooperatively formed by the platform 18 and retaining strap 20. As discussed above, a pair of catches 64 along with the base 46 and retaining strap 20 cooperatively form each of the respective openings. Furthermore, projections 38 are received respectively in the remaining oppositely spaced openings. Thus, the side edges 68 are configured to engage and restrict movement of the hub 34 relative to the platform 18. In this manner, the side edges 68, strap 20, and base 46 prevent the hub 34 from twisting or bending that would permit inadvertent removal of the hub 34 from within the platform 18.

Again, the fully attached retaining strap 20 is preferably elastically elongated and under tension to force the catheter 12 against the platform 18. Additional details of how the platform 18 and retaining strap 20 operate to secure catheters in various orientations are further disclosed in the above incorporated Application. While the above described platform 18 and strap 20 include features that are important with respect to some aspects of the present invention, it is entirely consistent with the principles of the present invention to use other types of catheter anchoring components not depicted in the embodiments disclosed herein. Moreover, the present invention is ideally suited for attaching other types of catheter anchoring components.

Turning back to FIGS. 1-4, the patient-contacting strip 16 is an adhesive-backed membrane that includes a substrate 86. The substrate 86 is cut to have an elongated shape and includes ends 88 and recessed sides 90 extending longitudinally between the ends 88. The ends 88 each include two extended portions 92 and recessed scallops 94 between the pair of extended portions 92. The shape of the illustrated strip 16 is intended for ornamental purposes and is the subject of co-pending U.S. Design patent application Ser. No. 29/253,412, filed Feb. 6, 2006, and entitled ADHESIVE PATIENT-CONTACT STRIP FOR INTRAVENOUS CATHETER ANCHORING DEVICES, which is hereby incorporated by reference herein. The substrate 86 is preferably formed of a flexible and permeable material, although partial permeability of the substrate is contemplated by the present invention. More preferably, the substrate 86 is formed of a fabric material. Furthermore, the substrate 86 preferably has a thickness T of about 0.005 to 0.015 inches. More preferably, the substrate thickness is about 0.008 inches. The very small thickness of the illustrated substrate 86 enhances the flexibility of the strip 16 so that the patient can comfortably wear the anchoring assembly 10 over a period of days or weeks.

The preferred substrate 86 also includes a surface energy of at least about 18 Dynes/cm or greater. More preferably, the substrate 86 includes a surface energy of about 43 Dynes/cm. A substrate's surface energy refers to the molecular force of attraction between the substrate and an adhesive (i.e., a high surface energy equates with a high attraction force). Most preferably, the substrate 86 includes polyester filaments that form interstices in the substrate 86 for receiving adhesive as will be discussed further below. Furthermore, the most preferred material is a non-woven tricot fabric. However, the principles of the present invention are equally applicable to the strip 16 including other woven or non-woven fabrics that are flexible and are thereby suitable for use as a patient-contacting strip.

The strip 16 further includes a skin-contacting adhesive layer 96 (see FIGS. 1 and 5) coated over a lower side 98 of the substrate 86. The adhesive layer 96 is preferably a pressure-sensitive adhesive ("PSA") including an acrylic resin material and is suitable for adhering itself to the substrate 86 as well as being removably adherent to human skin. More preferably, the adhesive layer 96 is provided with the substrate 86 as a pre-assembled adhesive-backed membrane. The substrate 86 and adhesive layer 96 cooperatively permit the strip 16 to be flexible and thereby suitable for removable attachment to the skin of the patient. One preferred Tricot fabric and a preferred adhesive layer are incorporated into an adhesive-backed membrane sold under the designation "BIOFLEX®" by Scapa North America, 111 Great Pond Drive, Windsor, Conn. 06095. However, the principles of the present invention are applicable to the use of other adhesives for removably adhering the substrate to skin.

Turning to FIGS. 2 and 3, the release liners 24 are preferably made of kraft paper and include two sections 100 that are folded onto each other to form a fold end 102 (see FIG. 3). Each of the release liners 24 is attached to the adhesive, layer 96 along one of the respective sections 100 so that the fold ends 102 are adjacent and the release liners 24 slightly overlap. The release liners 24 preferably completely cover the adhesive layer 96. The unattached sections 100 provide convenient pull-tabs for removal of the respective release liners 24. In this manner, the adhesive layer 96 may be exposed in a relatively sterile manner just prior to adhering the strip 16 to the patient's skin.

Figure 5:
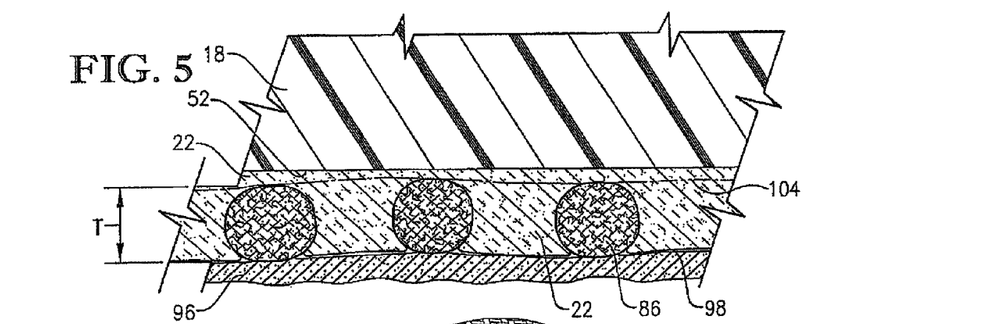
FIG. 5 is an enlarged partial cross-sectional elevational view of the intravenous catheter anchoring device of FIGS. 1-4.

Turning to FIGS. 3-5, the intermediate adhesive layer 22 is applied to an upper side 104 of the substrate 86. Preferably, the adhesive layer 22 is a hot-melt adhesive which generally does not include solvent. Thus, the hot-melt adhesive can be repetitively softened by heat and solidified by cooling. One exemplary hot-melt adhesive is designated as Bostik HM 4229, which is a thermoplastic dimer-acid polyamide, and is manufactured by Bostik Findley, Inc., 211 Boston Road, Middleton, Mass. 01949. This adhesive has thermosel viscosity values as follows: at 160° C. the value is 27,800, at 180° C. the value is 11,600, at 200° C. the value is 5,975, at 225° C. the value is 2850, and at 250° C. the value is 1525. Furthermore, the Bostik adhesive has a Shore A Hardness value of 75 and a B&R Softening Point of 138° C. The Bostik adhesive is typically applied at ranges of about 180-204° C.

The adhesive layer 22 is preferably adherent to a low surface energy substrate material, such as the material of the preferred substrate 86 above. An adhesive that is applied to a low surface energy substrate will not "flow" (i.e., wet-out or spread out) along the substrate as readily as an adhesive that is applied to a high surface energy substrate. In addition, the composition of the adhesive and the ambient conditions also affect the adhesive's flowability. Preferably, the adhesive layer 22 is adherent to a substrate material with a surface energy of at least about 18 Dynes/cm or greater.

The adhesive layer 22, when set, is a highly flexible but solid material that is die-cut to closely follow the shape of the platform 18 in order to maximize the bonded surface area between the platform 18 and the substrate 86. However, it is consistent with the principles of the present invention that the adhesive layer 22 could be applied in a form more similar to a liquid and could be applied by pouring or spraying methods known to those of ordinary skill in the art. Moreover, the preferred adhesive material forming layer 22 has highly cohesive qualities for adhering different materials to one another, which in the preferred embodiment includes the hard plastic forming the platform 18 and the non-woven tricot fabric forming the strip 16.

Referring again to FIG. 2, the platform 18 is arranged so that the sides 70 are spaced adjacent to respective recessed sides 90 of the strip 16. The platform 18 is bonded to the substrate 86 of strip 16 with the adhesive layer 22. The preferred construction is perhaps more detailedly illustrated in FIGS. 4 and 5. In particular, with regard to the first preferred embodiment, the adhesive layer 22 is bonded to the lower surface 52 of the platform 18 and the upper side 104 of the substrate 86. As mentioned previously, the substrate 86 includes filaments that form interstices therein. The adhesive layer 22 becomes mechanically interlocked with the strip 16 by solidifying within the interstices and surrounding at least some of the filaments.

Turning to FIGS. 3-5, the preferred hot-melt adhesive layer 22 is preferably flowable from the upper side 104 into the interstices to a depth greater than half the thickness T in order to become fully mechanically interlocked with the substrate 86 (e.g., where the adhesive layer 22 is "wedged" between and at least slightly under adjacent fibers of the substrate 86, as is best shown in FIG. 5). In the illustrated embodiment, a portion of the adhesive layer 22 remains spaced above the upper side 104 (see FIGS. 4 and 5). However, the principles of the present invention are applicable where the adhesive layer 22 is entirely absorbed within the substrate 86 and contacts the adhesive layer 96.

More preferably, the adhesive layer 22 flows from the upper side 104 into close proximity with the lower side 98 so as to optimize the mechanical interengagement with the substrate 86. Most preferably, the adhesive layer 22 does not penetrate through the adhesive layer 96 so as to contact the release liners 24. Thus, while the adhesive layer 22 preferably remains spaced from and does not contact the adhesive layer 96, the principles of the present invention are applicable where the adhesive layer 22 in fact contacts at least part of the adjacent side of adhesive layer 96. Thus, the composition of the layers 22,96 prevents the closely adjacent layers 22,96 from mixing with each other or the layer 22 from penetrating the layer 96. The spacing and composition of the layers 22,96 also prevents the adhesive layer 22 from becoming disposed onto the release liners 24, which may adversely change the otherwise temporary bond between the adhesive layer 96 and release liners 24. The principles of the present invention are also applicable to other configurations of the adhesive layer 22 or strip 16 so that the adhesive layer 22 is restricted from permeating completely through the strip's thickness or otherwise penetrating through the adhesive layer 96. For example, the strip 16 could include an impermeable section spaced between adhesive layers 22,96 to prevent flow of the adhesive layer 22 up to adhesive layer 96.

Turning again to FIGS. 1-4, the adhesive layer 22 and strip 16 are configured so that the anchoring assembly 10 is comfortable for a patient. Particularly, the use of a very thin strip 16 and the highly flexible adhesive layer 22, as discussed above, enables the strip 16 to be more comfortably worn by the patient. While the illustrated strip 16 has a thickness that would normally allow adhesive to permeate completely through the strip 16 and adversely affect bonding of the strip 16 to the release liner 24, the characteristics of the adhesive layer 22 and the strip 16 permit the adhesive layer 22 to be applied and solidified without permeating completely through the adhesive layer 96. Moreover, it has been determined that the use of hot melt adhesive provides the desired adhesion between the platform 18 and strip 16 while permitting the strip 16 to be coated with Teflon®. Such coating ensures that the strip 16 retains a pristine condition and does not absorb blood during use.

The combined platform 18 and strip 16 are removably attachable to the patient's skin as discussed above. The strip 16 and adhesive layer 22 flex to conform to curved surfaces in the attachment site. Furthermore, the contoured shape of the relatively rigid platform 18 permits the platform 18 to remain bonded to the strip 16 while being closely arranged to the patient's skin even if it includes significant curvature.

Figure 6:
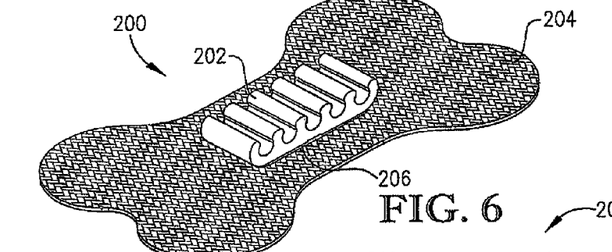
FIG. 6 is a perspective view of a second embodiment of the intravenous catheter anchoring device showing a tubing collector that is adhered to the patient with a permeable adhesive strip.
Figure 7:
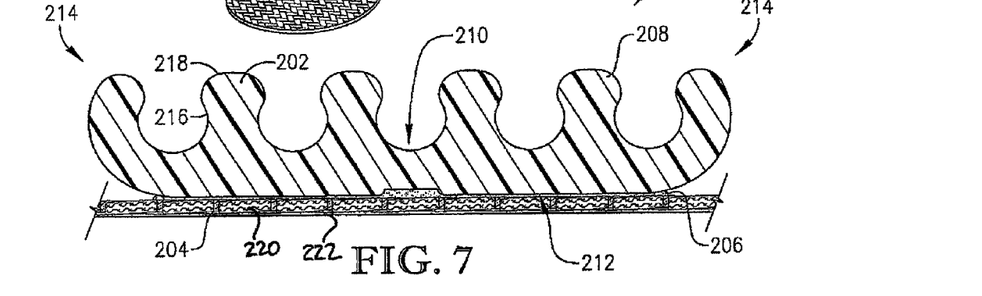
FIG. 7 is a cross-sectional elevational view of the intravenous catheter anchoring device of FIG. 6.

FIGS. 6-7 illustrate an alternative embodiment of the present invention. For purposes of brevity, primarily the differences of the alternative embodiment from the first embodiment will be described.

Turning to FIG. 6, an alternative intravenous catheter anchoring assembly 200 includes an alternative platform 202 adhesively attached to a strip 204 by an intervening adhesive layer 206. The illustrated platform 202 is a tubing collector including a body 208 presenting upper and lower surfaces 210,212 (see FIG. 7). The body 208 further includes ends 214 with arcuate troughs 216 spaced between the ends and separated by ridges 218. The troughs 216 receive tubing (not shown).

Turning to FIG. 7, the strip 204 includes a fabric substrate 220 and a skin-contacting adhesive layer 222 made of a pressure sensitive adhesive. The illustrated adhesive layer 206 is located between the platform 202 and strip 204 and also is flowable substantially through the substrate 220 in order to become fully mechanically interlocked with the substrate 220. Thus, the preferred adhesive layer 206 is flowable into the interstices so as to be closely adjacent the skin-contacting adhesive layer 222 without penetrating the adhesive layer 222. In this manner, the adhesive layer 206 is restricted from attaching to the release liner (not shown).

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An anchor pad comprising:
a flexible strip including a plurality of interstices therein and presenting first and second opposite surfaces, said strip having a thickness from said first surface to said second surface of about 0.005 to 0.015 inches and being liquid permeable from said first surface to said second surface, said strip being configured to be removably attached to the patient along said first surface;
a skin-contacting adhesive layer disposed on at least a portion of said first surface; and
an adhesive material adhered to said strip along a wetted portion of said second surface, said adhesive material being flowable prior to being solidified, said adhesive material extending from said wetted portion into at least some of said interstices so that said adhesive material becomes solidified therein, said adhesive material being entirely spaced from said adhesive layer of said strip when solidified so that said adhesive material does not mix with said adhesive layer.

2. The pad as claimed in claim 1 further comprising a release liner removably attached to said first surface of said strip.

3. The pad as claimed in claim 1, wherein said adhesive material comprises a hot-melt adhesive.

4. The pad as claimed in claim 3, wherein said hot-melt adhesive comprises thermoplastic polyamide.

5. The pad as claimed in claim 1, wherein said strip includes a polyester substrate.

6. The pad as claimed in claim 1, wherein said adhesive material remains flexible after being solidified.

7. The pad as claimed in claim 1, wherein said strip comprises a non-woven tricot fabric substrate.

8. The pad as claimed in claim 7, wherein said substrate includes filaments forming interstices therebetween, said adhesive material mechanically interlocking with at least some of said filaments.

9. The pad as claimed in claim 8, wherein said adhesive material extends a depth greater than about half the thickness of said strip.

10. The pad as claimed in claim 1, wherein said adhesive material is spaced entirely from said skin-contacting adhesive layer.

11. An anchor pad comprising:
a flexible strip having a thickness from a first surface to a second opposite surface of about 0.005 to 0.015 inches, said strip being liquid permeable from said first surface to said second surface, said strip being configured to be removably attached to a patient along said first surface;
a skin-contacting adhesive layer disposed on at least a portion of said first surface; and
an adhesive material adhered to said strip along a wetted portion of said second surface, said adhesive material being flowable prior to being solidified and extending from said wetted portion of said second surface into said strip, said adhesive material being entirely spaced from said adhesive layer of said flexible strip when solidified.

12. The device as claimed in claim 11 further comprising a release liner removably attached to said first surface of said strip.

13. The pad as claimed in claim 11, wherein said adhesive material comprises a hot-melt adhesive.

14. The pad as claimed in claim 11, wherein said strip includes a polyester substrate.

15. The pad as claimed in claim 11, wherein said adhesive material remains flexible after being solidified.

16. A pad comprising:
a flexible strip presenting first and second opposite surfaces, said strip having a thickness from said first surface to said second surface of about 0.005 to 0.015 inches and being liquid permeable from said first surface to said second surface, said strip being configured to be removably attached to a patient along said first surface;
a skin-contacting adhesive layer adhered to at least a portion of said first surface;
a release liner removably attached to at least a portion of said first surface; and
an adhesive material located between said release liner and said strip, said adhesive material being adhered to said strip along said second surface.

17. The pad as claimed in claim 16, wherein said adhesive material comprises hot-melt adhesive.

18. The pad as claimed in claim 16, wherein said adhesive material is spaced from said release liner when solidified.

19. The pad as claimed in claim 16, wherein said adhesive material is spaced from said adhesive layer.

20. The pad as claimed in claim 16, wherein said strip has a thickness from said first surface to said second surface of about 0.008 inches.

* * * * *